(12) United States Patent
Koh et al.

(10) Patent No.: US 9,883,808 B2
(45) Date of Patent: Feb. 6, 2018

(54) PHOTO-ACOUSTIC IMAGING APPARATUS AND METHOD OF DISPLAYING PHOTO-ACOUSTIC IMAGES

(71) Applicant: SAMSUNG MEDISON CO., LTD., Gangwon-do (KR)

(72) Inventors: Dal-Kwon Koh, Gangwon-do (KR); Jung-Taek Oh, Seoul (KR); Jung-Ho Kim, Gangwon-do (KR); Jong-Kyu Jung, Gangwon-do (KR)

(73) Assignee: SAMSUNG MEDISON CO., LTD., Hongcheon-gun, Gangwon-Do (KR)

( * ) Notice: Subject to any disclaimer, the term of this patent is extended or adjusted under 35 U.S.C. 154(b) by 368 days.

(21) Appl. No.: 14/548,262

(22) Filed: Nov. 19, 2014

(65) Prior Publication Data
US 2015/0201843 A1 Jul. 23, 2015

(30) Foreign Application Priority Data

Jan. 17, 2014 (KR) .................. 10-2014-0006265

(51) Int. Cl.
*A61B 5/00* (2006.01)
*A61B 5/1455* (2006.01)
*A61B 5/1495* (2006.01)

(52) U.S. Cl.
CPC .......... *A61B 5/0095* (2013.01); *A61B 5/1495* (2013.01); *A61B 5/14552* (2013.01); *A61B 5/7271* (2013.01)

(58) Field of Classification Search
None
See application file for complete search history.

(56) References Cited

U.S. PATENT DOCUMENTS

| 2004/0054268 A1* | 3/2004 | Esenaliev | A61B 5/0095 600/322 |
| 2005/0004458 A1* | 1/2005 | Kanayama | A61B 5/0091 600/437 |

(Continued)

FOREIGN PATENT DOCUMENTS

| JP | 3779410 B2 | 5/2006 |
| JP | 4664209 B2 | 4/2011 |

(Continued)

OTHER PUBLICATIONS

Notification of Transmittal of The International Search Report and The Written Opinion of the International Searching Authority, or the Declaration issued in International Application No. PCT/KR2014/009419 dated Jan. 20, 2015.

(Continued)

*Primary Examiner* — Michael Kahelin
*Assistant Examiner* — Bradley Impink
(74) *Attorney, Agent, or Firm* — McDermott Will & Emery LLP (57) ABSTRACT

Provided are a photo-acoustic imaging apparatus and a method of displaying a photo-acoustic image by the photo-acoustic imaging apparatus. The method of displaying a photo-acoustic image by a photo-acoustic imaging apparatus includes: obtaining a first reception signal, which converts a first acoustic wave generated as light having a first wavelength is absorbed by a subject, and a second reception signal, which converts a second acoustic wave generated as light having a second wavelength is absorbed by the subject; determining a first correction coefficient for the first reception signal and a second correction coefficient for the second reception signal based on a ratio between a size of the first reception signal and that of the second reception signal; and (Continued)

displaying a photo-acoustic image which is corrected based on the first and second correction coefficients.

19 Claims, 6 Drawing Sheets

(56) References Cited

U.S. PATENT DOCUMENTS

| | | | |
|---|---|---|---|
| 2006/0224053 A1* | 10/2006 | Black | A61B 5/0048 600/310 |
| 2008/0194929 A1 | 8/2008 | Pesach et al. | |
| 2011/0021924 A1* | 1/2011 | Sethuraman | A61B 5/0095 600/463 |
| 2011/0071598 A1 | 3/2011 | McKenna | |
| 2011/0106478 A1* | 5/2011 | Someda | A61B 5/0059 702/104 |
| 2013/0035570 A1 | 2/2013 | Miyasato | |
| 2013/0109941 A1 | 5/2013 | Li et al. | |
| 2013/0144150 A1 | 6/2013 | Kim | |
| 2013/0199299 A1 | 8/2013 | Wang et al. | |
| 2013/0289394 A1 | 10/2013 | Hielscher et al. | |
| 2013/0304405 A1 | 11/2013 | Schmid et al. | |
| 2014/0018645 A1 | 1/2014 | Wada et al. | |
| 2014/0296690 A1* | 10/2014 | Miyasato | A61B 5/0095 600/407 |
| 2015/0238090 A1* | 8/2015 | Suita | A61B 5/708 600/323 |
| 2016/0120412 A1* | 5/2016 | Suita | A61B 5/0095 73/606 |

FOREIGN PATENT DOCUMENTS

| | | |
|---|---|---|
| JP | 2012-217554 A | 11/2012 |
| JP | 2013-034852 A | 2/2013 |
| JP | 2013-048739 A | 3/2013 |
| JP | 2013-052227 A | 3/2013 |
| JP | 2013-545543 A | 12/2013 |

OTHER PUBLICATIONS

Aniruddha Ray et al., "Lifetime-based photoacoustic oxygen sensing in vivo", Journal of Biomedical Optics, May 2012, 17(5); 057004, pp. 1-6.

Extended European Search Report dated Jul. 12, 2017 issued in European Patent Application No. 14878543.9.

* cited by examiner

FIG. 8

PHOTO-ACOUSTIC IMAGING APPARATUS AND METHOD OF DISPLAYING PHOTO-ACOUSTIC IMAGES

RELATED APPLICATION

This application claims the benefit of Korean Patent Application No. 10-2014-0006265, filed on Jan. 17, 2014, in the Korean Intellectual Property Office, the disclosure of which is incorporated herein in its entirety by reference.

BACKGROUND

1. Field

One or more embodiments of the present invention relate to a photo-acoustic imaging apparatus and a method of displaying images by the photo-acoustic imaging apparatus, and more particularly, to a method and an apparatus for providing rather accurate results by correcting values received by the photo-acoustic imaging apparatus.

2. Description of the Related Art

Various medical imaging apparatuses have been used to examine an internal body structure of a subject and diagnose diseases. For example, apparatuses applying magnetic resonance imaging (MRI), computed tomography (CT), ultrasound, X-rays, and positron emission tomography (PET), etc. are used. In particular, as optical tomography technology that does not ionize tissues unlike other medical imaging technologies, a photo-acoustic imaging apparatus using a photo-acoustic effect, which shows an acoustic reaction after materials absorb light, is used.

If a multi-wavelength photo sound is used, oxygen saturation ($SpO_2$) can be measured. In this case, however, oxygen saturation values cannot be accurately measured due to various reasons such as actual wavelengths and a tissue state. For example, when cancers are chemically treated, oxygen saturation of cancer tissues and tissues around them is changed. In order to measure a change in the oxygen saturation, a variety of multi-wavelength photo-acoustic apparatuses are used, but it is difficult to measure accurate values.

SUMMARY

One or more embodiments of the present invention include a photo-acoustic imaging apparatus capable of accurately measuring oxygen saturation ($SpO_2$) through correction and a method of displaying a photo-acoustic image.

Additional aspects will be set forth in part in the description which follows and, in part, will be apparent from the description, or may be learned by practice of the presented embodiments.

According to one or more embodiments of the present invention, a method of displaying a photo-acoustic image by a photo-acoustic imaging apparatus, the method including: obtaining a first reception signal, which converts a first acoustic wave generated as light having a first wavelength is absorbed by a subject, and a second reception signal, which converts a second acoustic wave generated as light having a second wavelength is absorbed by the subject; determining a first correction coefficient for the first reception signal and a second correction coefficient for the second reception signal based on a ratio between a size of the first reception signal and that of the second reception signal; and displaying a photo-acoustic image which is corrected based on the first and second correction coefficients.

The determining the first and second correction coefficients may include: obtaining an oxygen saturation value of the subject, which is measured by an oxygen saturation measuring instrument; determining a standard ratio with regard to the size of the first reception signal and that of the second reception signal based on the oxygen saturation value; and determining the first and second correction coefficients which correct the ratio between the size of the first reception signal and that of the second reception signal based on the determined standard ratio.

The obtaining the first reception signal and the second reception signal may further include selecting the subject included in an image displayed through the photo-acoustic imaging apparatus.

The method may further include displaying a window which displays the subject included in the image and displayed through the photo-acoustic imaging apparatus as the subject is selected.

The displaying the corrected photo-acoustic image may include simultaneously displaying the corrected photo-acoustic image along with at least one of a B-mode ultrasound image, a C-mode ultrasound image, an oxygen saturation display image, and a signal characteristic image.

The displaying the corrected photo-acoustic image may include displaying the corrected photo-acoustic image along with the determined first and second correction coefficients.

The displaying the corrected photo-acoustic image may further include displaying a light source error message in a case where at least one of the first correction coefficient and the second correction coefficient exceeds a reference range.

The displaying the corrected photo-acoustic image may further include: setting a region of interest; and displaying the photo-acoustic image, which corresponds to the set region of interest, on the region of interest.

The determining the first and second correction coefficients may include determining the first and second correction coefficients based on a degree in which light of the first wavelength and the second wavelength, which is emitted from skin tissues, has influence on the generation of acoustic waves according to a depth of the subject.

According to one or more embodiments of the present invention, a photo-acoustic imaging apparatus includes: a first light source emitting light having a first wavelength; a second light source emitting light having a second wavelength; a signal reception unit which obtains a first reception signal based on a first acoustic wave generated as light emitted from the first light source is absorbed by a subject, and obtains a second reception signal based on a second acoustic wave generated as light emitted from the second light source is absorbed by the subject; and a display unit which determines a first correction coefficient for the first reception signal and a second correction coefficient for the second reception signal based on a ratio between a size of the first reception signal and that of the second reception signal, and displays a photo-acoustic image that is corrected based on the first and second correction coefficients.

The display unit may determine the first correction coefficient and the second correction coefficient which obtain an oxygen saturation value of the subject, which is measured by an oxygen saturation measuring instrument, determine a standard ratio with regard to the size of the first reception signal and that of the second reception signal based on the oxygen saturation value, and correct the ratio between the size of the first reception signal and that of the second reception signal based on the determined standard ratio.

The photo-acoustic imaging apparatus may further include a subject selection unit which selects the subject included in an image displayed through the display unit.

The display unit may display a window which displays the selected subject when the subject is selected by the subject selection unit.

The display unit may display the corrected photo-acoustic image together with at least one of a B-mode ultrasound image, a C-mode ultrasound image, an oxygen saturation display image, and a signal characteristic image.

The display unit may display the corrected photo-acoustic image together with the determined first and second correction coefficients.

The display unit may display a light source error message when at least one of the first correction coefficient and the second correction coefficient exceeds a reference ratio.

The photo-acoustic imaging apparatus may further include a region of interest selection unit which sets a region of interest. The display unit may display the photo-acoustic image, which corresponds to the set region of interest, on the region of interest when the region of interest is set by the region of interest selection unit.

The display unit may determine the first and second correction coefficients based on a degree in which light of the first wavelength and the second wavelength, which is emitted from skin tissues, has influence on the generation of acoustic waves according to a depth of the subject.

According to one or more embodiments of the present invention, there is provided a computer-readable recording medium having recorded a program thereon for executing the method of displaying a photo-acoustic image by a photo-acoustic imaging apparatus.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, expressions such as "at least one of", when preceding a list of elements, modify the entire list of elements and do not modify the individual elements of the list.

Throughout the specification, when a portion is "connected" to another portion, the portion may be "directly connected" to the other portion, and also the portion may be "electrically connected" to the other portion by interposing a device therebetween. Also, when a portion "includes" an element, another element may be further included, rather than excluding the existence of the other element, unless otherwise described.

Of body parts, breasts have soft tissues and are exposed to the outside. Thus, a shape of the breasts may severely change due to gravity, pressure, or the like. Therefore, images of the breasts will be a main example of the present invention. However, the present invention is not limited thereto, and may be applied to other medical images.

Hereinafter, the present invention will be described in detail by explaining exemplary embodiments of the invention with reference to the attached drawings.

Figure 1:
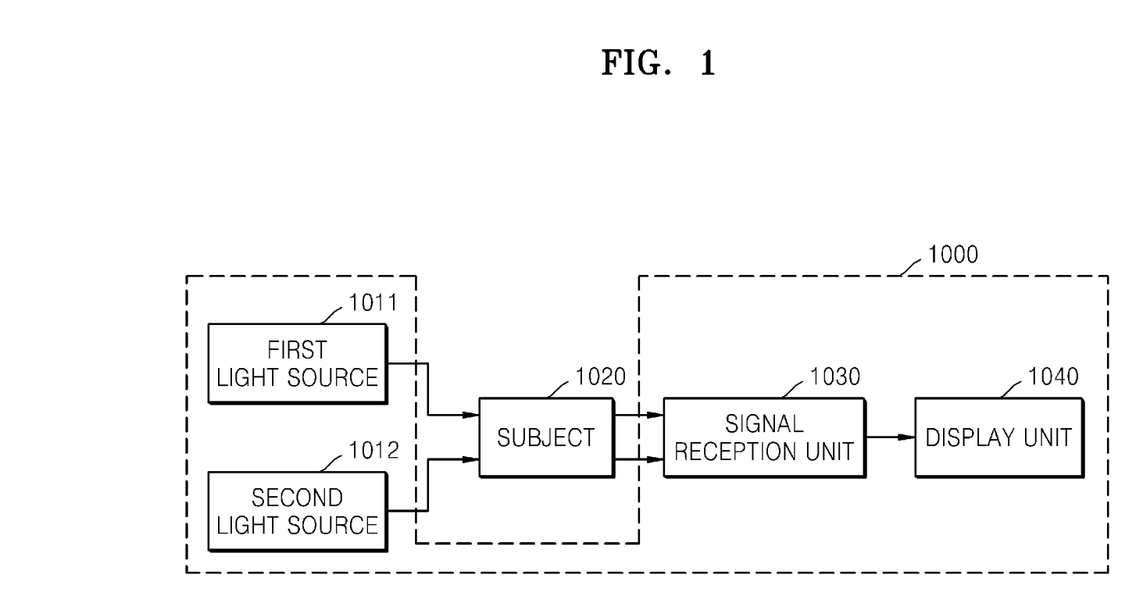
FIG. 1 is a structural view of a photo-acoustic imaging apparatus according to an embodiment of the present invention.

FIG. 1 is a structural view of a photo-acoustic imaging apparatus 1000 according to an embodiment of the present invention.

The photo-acoustic imaging apparatus 1000 may include a first light source 1011, a second light source 1012, a signal reception unit 1030, and a display unit 1040. FIG. 1 is a view for explaining an embodiment, and the photo-acoustic imaging apparatus 1000 may include more or less components than the components illustrated in FIG. 1. Also, the components of FIG. 1 may be replaced by other components that perform the same functions as the components illustrated in FIG. 1.

The first light source 1011 may emit light having a first wavelength. Also, the second light source 1012 may emit light having a second wavelength. The first wavelength and the second wavelength may be different. According to the present embodiment, the first and second light sources 1011 and 1012 may each include a semiconductor for emitting laser, but are not limited thereto.

The first light source 1011 and the second light source 1012 may each further include an amplifier (not shown) for amplifying energy of light emitted by the first light source 1011 and the second light source 1012. The amplifier (not shown) may be an optical fiber amplifier for amplifying light.

When the light emitted by the first light source 1011 and the second light source 1012 is absorbed by a subject 1020, the subject 1020 emits energy of the absorbed light and generates acoustic waves. The signal reception unit 1030 detects a first acoustic wave, which is generated as the light emitted by the first light source 1011 is absorbed by the subject 1020, and may convert the detected first acoustic wave into a first reception signal. Also, the signal reception unit 1030 detects a second acoustic wave, which is generated as the light emitted by the second light source 1012 is absorbed by the subject 1020, and may convert the detected second acoustic wave into a second reception signal. Here, the first and second acoustic waves may be ultrasound. In the specification, the photo-acoustic imaging apparatus 1000 includes two light sources, but, according to some embodiments, may include a plurality of light sources.

The display unit 1040 may generate a photo-acoustic image and display the generated photo-acoustic image based on the first and second reception signals. The display unit 1040 may include a processor for processing image data and a display medium for outputting images.

The photo-acoustic imaging apparatus 1000 may further include a subject selection unit (not shown) capable of selecting the subject 1020 from among subjects included in the photo-acoustic image. For example, referring to FIG. 2, the subject selection unit (not shown) may select a subject 2010 based on information that is input by a user by using an input device (not shown). The input device (not shown) may be variously configured as a track ball, a mouse, a keypad, or a combination thereof. Alternatively, the subject selection unit (not shown) may automatically detect the subject 2010 by using image recognition regarding the photo-acoustic image.

Figure 2:
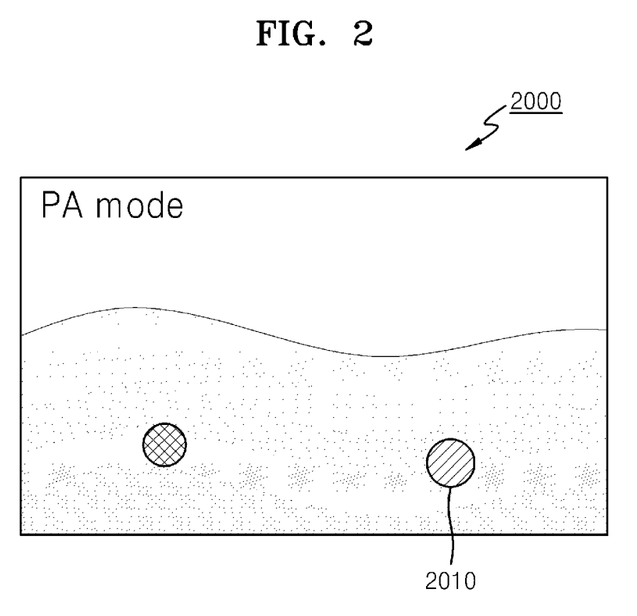
FIG. 2 is a view of a photo-acoustic image according to an embodiment of the present invention.
Figure 3:
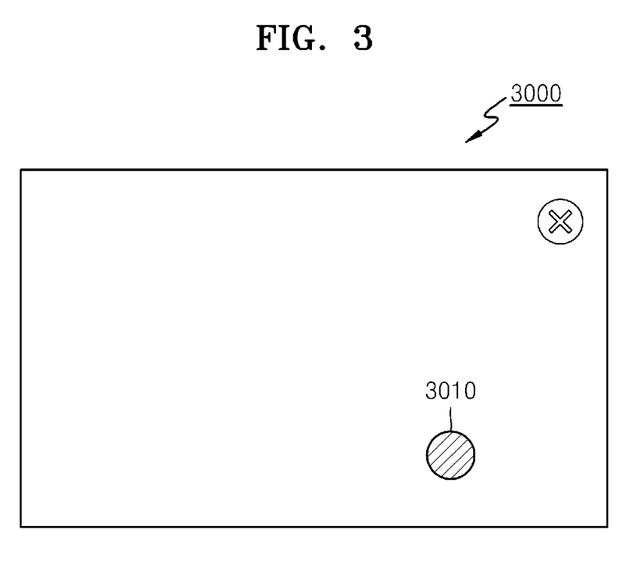
FIG. 3 is a view of a user interface which displays a selected subject, according to an embodiment of the present invention.

When the subject 2010 is selected as shown in FIG. 2, the display unit 1040 may display a window 3000 in order to highlight and display the selected subject 2010, as illustrated in FIG. 3. The window 3000 may include a subject 3010. FIG. 3 is a view of a user interface which displays a selected subject, according to an embodiment of the present invention. A user interface for highlighting and displaying the subject 3010 may be variously configured.

Referring back to FIG. 1, the display unit 1040 may determine a signal ratio of the first reception signal and the second reception signal. In addition, the display unit 1040 may determine correction coefficients corresponding to the first and second reception signals based on the determined signal ratio. When the correction coefficients are determined, the display unit 1040 corrects a photo-acoustic image based on the determined correction coefficients, and may display the corrected photo-acoustic image. When a user interface for highlighting and displaying selected subjects, for example, the window 3000 of FIG. 3, is terminated, the display unit 1040 may display the corrected photo-acoustic image according to the correction coefficients determined with regard to the selected subjects. Throughout the specification, the correction coefficients may denote values for correcting photo-acoustic images by correcting fluence of each wavelength.

In an embodiment, the subject 1020 may be arteries. In the case of arteries, the fluence of a wavelength is determined according to oxygen saturation. The oxygen saturation may be transmitted by a separate oxygen saturation measuring instrument (not shown) or may be obtained based on an oxygen saturation measuring instrument (not shown) included in the photo-acoustic imaging apparatus 1000.

Figure 4:
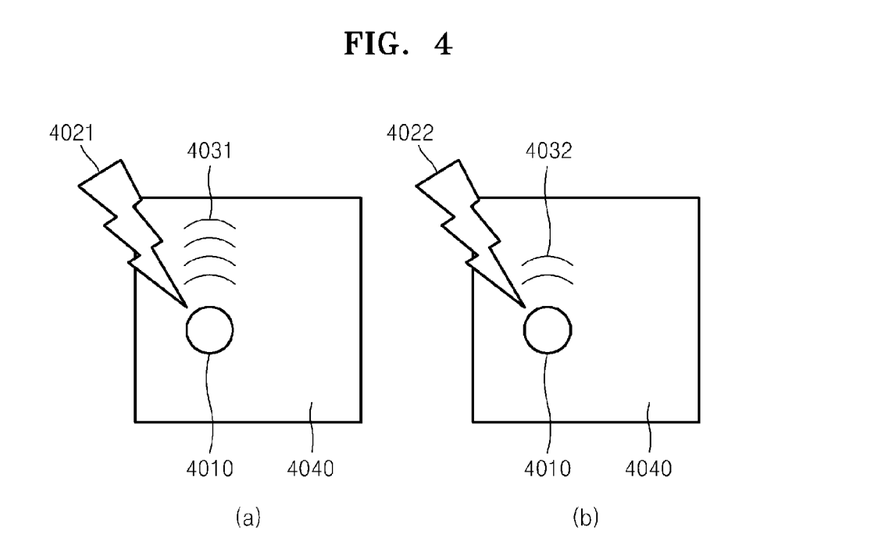
FIGS. 4A and 4B are views showing photo-acoustic effects according to an embodiment of the present invention.

Referring to FIGS. 4A and 4B, the display unit 1040 may determine a signal ratio of the first reception signal corresponding to a first acoustic wave 4031 that is emitted by an artery 4010 absorbing light having a first wavelength 4021 and of the second reception signal corresponding to a second acoustic wave 4032 that is emitted by the artery 4010 absorbing light having a second wavelength 4022. Also, the display unit 1040 may compare a reference ratio of the first and second reception signals according to the oxygen saturation with the determined signal ratio. The display unit 1040 may determine the correction coefficients for correcting the determined signal ratio by using the reference ratio. The display unit 1040 corrects the photo-acoustic image with regard to tissues 4040 based on the determined correction coefficients, and may display the corrected photo-acoustic image. For example, when the oxygen saturation is 95%, the reference ratio corresponding to the oxygen saturation of 95% is 0.9:0.8 and the measured signal ratio is 0.9:0.4, the display unit 1040 may determine a correction coefficient which doubles the second reception signal in comparison with the first reception signal so as to correct the signal ratio to 0.9:0.8.

According to another example, the subject 1020 may be a material injected into body tissue during a surgical operation. The material injected into the body tissue may be carbon. A carbon tattoo has a high light absorption rate, and thus a photo-acoustic signal is proportional to the fluence, not the light absorption rate. Therefore, if the subject 1020 is the carbon tattoo injected into the body tissue, the reference ratio to each reception signal becomes 1:1. Based on the reference ratio, the display unit 1040 determines the correction coefficients and may correct the photo-acoustic image based on the determined correction coefficients.

The above-described reference ratio is an example, and the reference ratio may vary according to embodiments. Also, according to an embodiment, the display unit 1040 may determine the correction coefficients as the user interface illustrated in FIG. 3 is terminated and may display the corrected photo-acoustic image.

FIGS. 5A through 5C are views showing a relation between a depth of tissues 5020 of a subject 5010 and fluence, according to an embodiment of the present invention.

Figure 5:
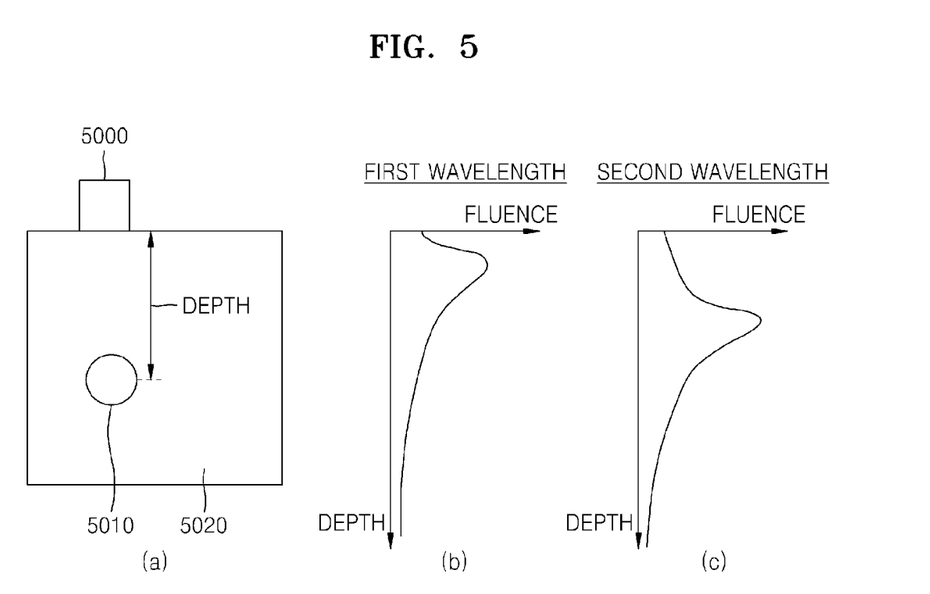
FIGS. 5A through 5C are views showing a relation between a depth of a subject's tissues and fluence, according to an embodiment of the present invention.

The fluence of light may change according to the depth from a light source 5000 to tissues 5020 of the subject 5010. In addition, the change of the fluence may be different according to a wavelength of the light, as illustrated in FIG. 5. Therefore, the display unit 1040 determines the depth from the light source 5000 to the tissues 5020 of the subject 5010 and may determine a correction coefficient in consideration of the determined depth.

Figure 6:
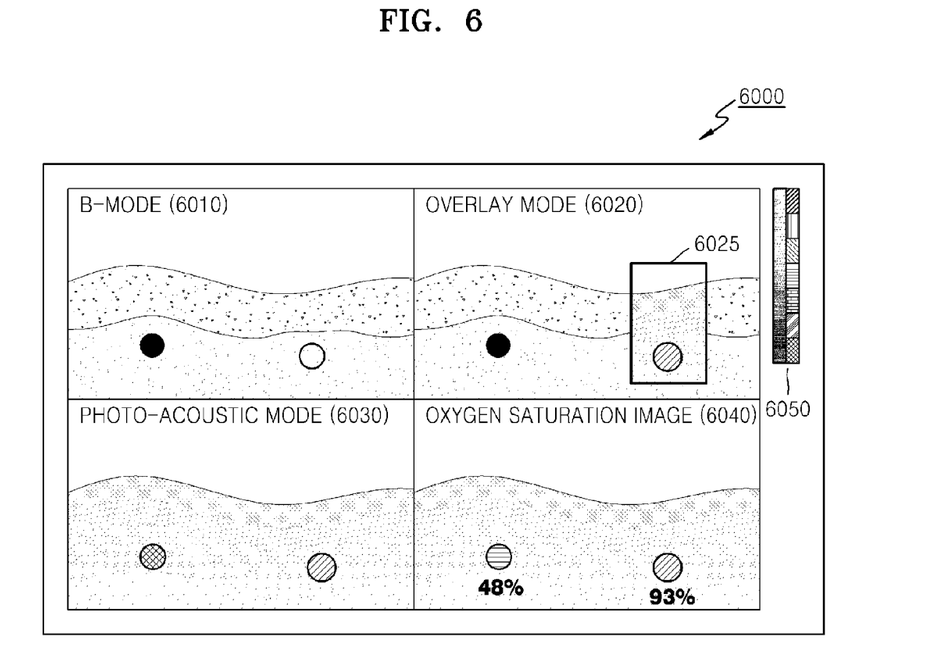
FIG. 6 is a view of a displayed image according to an embodiment of the present invention.

FIG. 6 is a view of a displayed image according to an embodiment of the present invention.

According to the embodiment, the display unit 1040 may simultaneously display a photo-acoustic image 6030 with at least one of a B-mode ultrasound image 6010, an oxygen saturation image 6040, a C-mode ultrasound image (not shown), and a signal characteristic image (not shown). Also, the display unit 1040 may display the photo-acoustic image 6030 together with an overlay image 6020 in which the B-mode ultrasound image 6010 is overlaid with the photo-acoustic image 6030. Here, the B-mode ultrasound image 6010 may be a two-dimensional (2D) image. Also, the C-mode ultrasound image (not shown) may be a three-dimensional (3D) image. The signal characteristic image (not shown) may be an image which displays a characteristic of a signal thereon. The oxygen saturation image 6040 may be an image which displays the oxygen saturation of tissues within a display range of the image. The overlay image 6020 may be an image which displays the photo-acoustic image 6030 in a region of interest 6025 that is set based on a user input or image recognition. The display unit 1040 according to the present embodiment may display a multiple view 6000 shown in FIG. 6.

Another image displayed with the photo-acoustic image 6030 may be displayed based on a color map that is different from that of the photo-acoustic image 6030. In addition, the display unit may simultaneously display a color bar 6050 corresponding to the color map used to display the photo-acoustic image 6030.

Figure 7:
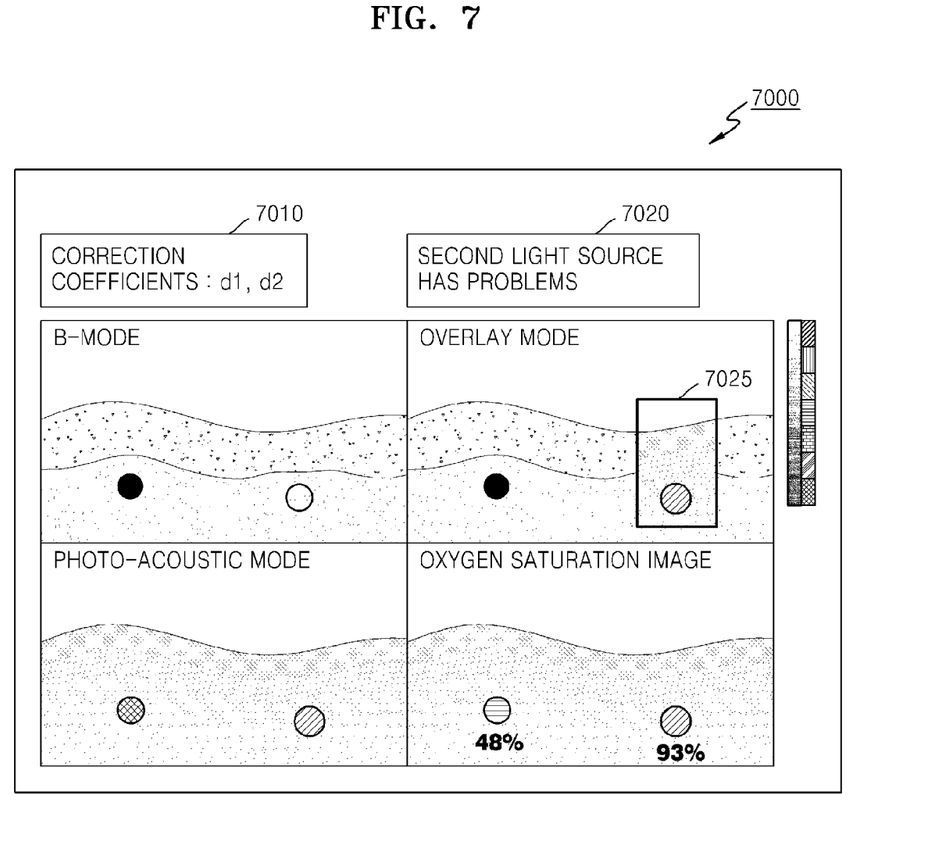
FIG. 7 is a view of a displayed image according to another embodiment of the present invention.

FIG. 7 is a view of a displayed image according to another embodiment of the present invention.

The display unit of the photo-acoustic imaging apparatus may simultaneously display a correction coefficient 7010 and an image including a photo-acoustic image. The photo-acoustic imaging apparatus may determine whether there is any problem in a light source of the photo-acoustic imaging apparatus based on a value of a determined correction coefficient. When it is determined that the light source has a problem, the display unit of the photo-acoustic imaging apparatus may display a light-source error message 7020 at the same time.

The photo-acoustic imaging apparatus may provide a user interface for setting a region of interest 7025 on an image. The display unit of the photo-acoustic imaging apparatus may overlap a photo-acoustic image, which corresponds to the image on which the region of interest 7025 is set, within the region of interest 7025.

Figure 8:
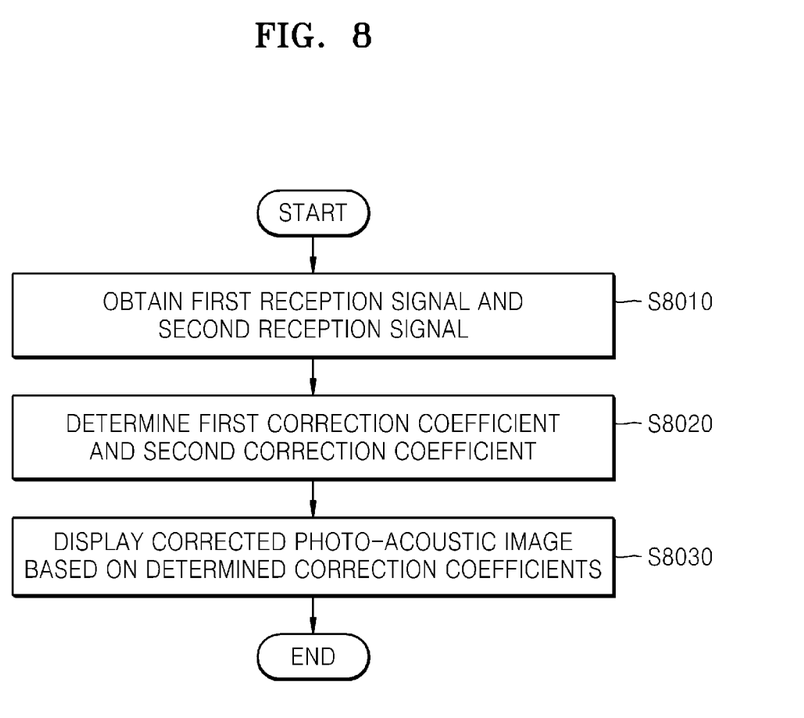
FIG. 8 is a flowchart of a process of displaying a photo-acoustic image, according to an embodiment of the present invention.

FIG. 8 is a flowchart of a process of displaying a photo-acoustic image, according to an embodiment of the present invention.

The photo-acoustic imaging apparatus may first obtain a first reception signal and a second reception signal (S8010). The first reception signal may be a signal generated by corresponding to light emitted by a first light source of the photo-acoustic imaging apparatus. In addition, the second reception signal may be a signal generated by corresponding to light emitted by a second light source of the photo-acoustic imaging apparatus. The light emitted by the first light source and the light emitted by the second light source may have different frequencies.

Then, the photo-acoustic imaging apparatus may determine a first correction coefficient and a second correction coefficient (S8020). The first and second correction coefficients may be determined based on a ratio of intensity of the first and second correction coefficients.

In operation S8020, the photo-acoustic imaging apparatus may obtain an oxygen saturation value of a subject measured by an oxygen saturation measuring instrument. The photo-acoustic imaging apparatus may determine a reference ratio to sizes of the first and second reception signals based on the oxygen saturation value. The reference ratio corresponding to the oxygen saturation value may be a preset value. The photo-acoustic imaging apparatus may determine the first and second correction coefficients in order to correct the ratio of the sizes of the first and second reception signals with the reference ratio.

According to another example, the photo-acoustic imaging apparatus may determine the first and second correction coefficients based on the reference ratio determined by selecting a subject having a fixed reference ratio. For example, when carbon injected into body tissues during a cancer surgery is selected as a subject, the reference ratio of the first and second reception signals becomes 1:1. In this case, operation S8020 may further include selecting a subject included in an image displayed through the photo-acoustic imaging apparatus. The photo-acoustic imaging apparatus may display a window which displays the subject included in the image displayed through the photo-acoustic imaging apparatus as the subject is selected.

According to a wavelength and a depth from skin tissues to the subject, correction coefficients may be determined based on a degree of influence on the generation of acoustic waves.

The photo-acoustic imaging apparatus may correct the photo-acoustic image based on the determined correction coefficients. The photo-acoustic imaging apparatus may display the corrected photo-acoustic image (S8030).

In operation S8030, the photo-acoustic imaging apparatus may display the corrected photo-acoustic image together with at least one of a B-mode ultrasound image, a C-mode ultrasound image, an oxygen saturation display image, and a signal characteristic image. Also, the photo-acoustic imaging apparatus may display the corrected photo-acoustic image together with at least one of a first correction coefficient, the second correction coefficient, and the light-source error message.

Furthermore, in operation S8030, the photo-acoustic imaging apparatus may set a region of interest on the at least one of the B-mode ultrasound image, the C-mode ultrasound image, the oxygen saturation display image, and the signal characteristic image according to a user input. The photo-acoustic imaging apparatus may overlap the set region of interest with some portion of the photo-acoustic image.

In the specification, the photo-acoustic imaging apparatus has two light sources, two reception signals, and two correction coefficients. However, according to embodiments, it would be obvious to one of ordinary skill in the art that the number of light sources, reception signals, and correction coefficients may vary.

In addition, other embodiments of the present invention can also be implemented through computer-readable code/instructions in/on a medium, e.g., a computer-readable medium, to control at least one processing element to implement any above-described embodiment. The medium can correspond to any medium/media permitting the storage and/or transmission of the computer-readable code.

The computer-readable code can be recorded/transferred on a medium in a variety of ways, with examples of the medium including recording media, such as magnetic storage media (e.g., ROM, floppy disks, hard disks, etc.) and optical recording media (e.g., CD-ROMs, DVDs, etc.), and transmission media such as Internet transmission media. Thus, the medium may be such a defined and measurable structure including or carrying a signal or information, such as a device carrying a bitstream according to one or more embodiments of the present invention. The media may also be a distributed network, so that the computer-readable code is stored/transferred and executed in a distributed fashion. Furthermore, the processing element could include a processor or a computer processor, and processing elements may be distributed and/or included in a single device.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A method of displaying a photo-acoustic image by a photo-acoustic imaging apparatus, the method comprising:
   obtaining a first reception signal, which converts a first acoustic wave generated as a result of light having a first wavelength being absorbed by a subject, and a second reception signal, which converts a second acoustic wave generated as a result of light having a second wavelength being absorbed by the subject;
   determining a ratio between an intensity of the first reception signal and an intensity of the second reception signal;
   comparing the determined ratio to a reference ratio and adjusting the intensity of the first reception signal and the intensity of the second reception signal until the determined ratio is equal to the reference ratio, wherein the adjusting includes applying a first correction coefficient to the first reception signal and applying a second correction coefficient to the second reception signal; and correcting a photo-acoustic image based on the first and second correction coefficients and displaying the corrected photo-acoustic image.

2. The method of claim 1, wherein the determining of the ratio between the intensity of the first reception signal and the intensity of the second reception signal comprises:
obtaining an oxygen saturation value of the subject, which is measured by an oxygen saturation measuring instrument; and
determining the ratio between the intensity of the first reception signal and the intensity of the second reception signal based on the oxygen saturation value.

3. The method of claim 1, wherein the subject is comprised in an image displayed through the photo-acoustic imaging apparatus; and
the obtaining the first reception signal and the second reception signal further comprises:
receiving a user input for selecting the subject; and
selecting the subject from the displayed image based on the user input.

4. The method of claim 3, further comprising displaying a window which displays the selected subject when the subject is selected.

5. The method of claim 1, wherein the displaying the corrected photo-acoustic image comprises simultaneously displaying the corrected photo-acoustic image along with at least one of a B-mode ultrasound image, a C-mode ultrasound image, and an oxygen saturation display image.

6. The method of claim 1, wherein the displaying the corrected photo-acoustic image comprises displaying the corrected photo-acoustic image along with the determined first and second correction coefficients.

7. The method of claim 1, wherein the displaying the corrected photo-acoustic image further comprises displaying a light source error message in a case where at least one of the first correction coefficient and the second correction coefficient is outside of a reference range.

8. The method of claim 1, wherein the displaying the corrected photo-acoustic image further comprises:
displaying at least one of a B-mode ultrasound image, a C-mode ultrasound image, and an oxygen saturation display image;
setting a region of interest on at least one of the B-mode ultrasound image, the C-mode ultrasound image, and the oxygen saturation display image; and
displaying the photo-acoustic image, which corresponds to the set region of interest, on the region of interest.

9. The method of claim 1, wherein the applying the first and second correction coefficients comprises adjusting the first and second correction coefficients based on a degree in which light of the first wavelength and the second wavelength has influence on the generation of acoustic waves according to a depth of the subject.

10. A photo-acoustic imaging apparatus comprising:
a first light source configured to emit light having a first wavelength;
a second light source configured to emit light having a second wavelength;
a signal receiver configured to obtain a first reception signal based on a first acoustic wave generated as a result of light emitted from the first light source being absorbed by a subject, and obtain a second reception signal based on a second acoustic wave generated as a result of light emitted from the second light source being absorbed by the subject;
a processor configured to:
determine a ratio between an intensity of the first reception signal and an intensity of the second reception signal,
compare the determined ratio to a reference ratio,
adjust the intensity of the first reception signal and the intensity of the second reception signal until the determined ratio is equal to the reference ratio, wherein the processor adjusts the intensity of the first reception signal and the intensity of the second reception signal by applying a first correction coefficient to the first reception signal and applying a second correction coefficient to the second reception signal, and
correct a photo-acoustic image based on the first and second correction coefficients; and
a display configured to display the corrected photo-acoustic image.

11. The photo-acoustic imaging apparatus of claim 10, wherein the processor:
obtains an oxygen saturation value of the subject, which is measured by an oxygen saturation measuring instrument; and
determines the ratio between the intensity of the first reception signal and the intensity of the second reception signal based on the oxygen saturation value.

12. The photo-acoustic imaging apparatus of claim 10, wherein the subject is comprised in an image displayed through the display,
the photo-acoustic imaging apparatus further comprises an input device configured to receive a user input for selecting the subject, and
the processor selects the subject from the displayed image based on the user input.

13. The photo-acoustic imaging apparatus of claim 12, wherein the display displays a window which displays the selected subject when the subject is selected.

14. The photo-acoustic imaging apparatus of claim 10, wherein the display displays the corrected photo-acoustic image together with at least one of a B-mode ultrasound image, a C-mode ultrasound image, and an oxygen saturation display image.

15. The photo-acoustic imaging apparatus of claim 10, wherein the display displays the corrected photo-acoustic image together with the determined first and second correction coefficients.

16. The photo-acoustic imaging apparatus of claim 10, wherein the display displays a light source error message when at least one of the first correction coefficient and the second correction coefficient is outside a reference range.

17. The photo-acoustic imaging apparatus of claim 10,
wherein the display displays the corrected photo-acoustic image together with at least one of a B-mode ultrasound image, a C-mode ultrasound image, and an oxygen saturation display image, and
the photo-acoustic imaging apparatus further comprises an input device configured to receive user input for selecting a region of interest in the at least one of the B-mode ultrasound image, the C-mode ultrasound image, and the oxygen saturation display image,
wherein the processor sets the region of interest in the at least one of the B-mode ultrasound image, the C-mode ultrasound image, and the oxygen saturation display image based on the user input, and wherein the display displays the photo-acoustic image, which corresponds to the set region of interest, on the region of interest.

18. The photo-acoustic imaging apparatus of claim 10, wherein the processor adjusts the first and second correction coefficients based on a degree in which light of the first wavelength and the second wavelength has influence on the generation of acoustic waves according to a depth of the subject.

19. A non-transitory computer-readable recording medium having recorded thereon a program that, when executed, causes a processor to perform the steps of:
    obtaining a first reception signal, which converts a first acoustic wave generated as a result of light having a first wavelength being absorbed by a subject, and a second reception signal, which converts a second acoustic wave generated as a result of light having a second wavelength being absorbed by the subject;
    determining a ratio between an intensity of the first reception signal and an intensity of the second reception signal;
    comparing the determined ratio to a reference ratio and adjusting the intensity of the first reception signal and the intensity of the second reception signal until the determined ratio is equal to the reference ratio, wherein the adjusting includes applying a first correction coefficient to the first reception signal and applying a second correction coefficient to the second reception signal; and
    correcting a photo-acoustic image based on the first and second correction coefficients and displaying the corrected photo-acoustic image.

\* \* \* \* \*